(12) United States Patent
Shankar

(10) Patent No.: US 6,963,779 B1
(45) Date of Patent: Nov. 8, 2005

(54) SYSTEM FOR THE SELECTIVE ACTIVATION OF FUNCTIONS IN AN IMPLANTABLE DEVICE BY A MAGNETIC FIELD

(75) Inventor: Balakrishnan Shankar, Valencia, CA (US)

(73) Assignee: Pacesetter, Inc., Sylmar, CA (US)

( * ) Notice: Subject to any disclaimer, the term of this patent is extended or adjusted under 35 U.S.C. 154(b) by 477 days.

(21) Appl. No.: 10/157,573

(22) Filed: May 28, 2002

(51) Int. Cl.⁷ ................................................ A61N 1/37
(52) U.S. Cl. ....................................................... 607/30
(58) Field of Search ...................................... 607/2–37

(56) References Cited

U.S. PATENT DOCUMENTS

| | | | |
|---|---|---|---|
| 6,080,187 A | 6/2000 | Alt et al. ...................... 607/32 |
| 6,101,417 A * | 8/2000 | Vogel et al. ................... 607/30 |
| 6,154,675 A | 11/2000 | Juran et al. .................... 607/29 |
| 6,163,725 A | 12/2000 | Peckham et al. ............. 607/61 |
| 6,240,316 B1 | 5/2001 | Richmond et al. ............ 607/42 |
| 6,334,071 B1 | 12/2001 | Lu ................................ 607/20 |
| 6,366,814 B1 | 4/2002 | Boveja et al. ................. 607/45 |
| 6,370,433 B1 | 4/2002 | Hartlaub et al. .............. 607/32 |
| 2003/0144704 A1 * | 7/2003 | Terry et al. .................... 607/27 |

* cited by examiner

Primary Examiner—Scott M. Getzow

(57) ABSTRACT

An implantable medical device that includes a magnetic sensor circuit that senses the presence of an external magnetic field and provides a signal that is proportionate to the strength of the magnetic field. The implantable medical device uses the variable signal to determine whether a magnetic field is being applied that is selected to activate a preselected function. In one implementation, the preselected function is a power up sequence.

29 Claims, 5 Drawing Sheets

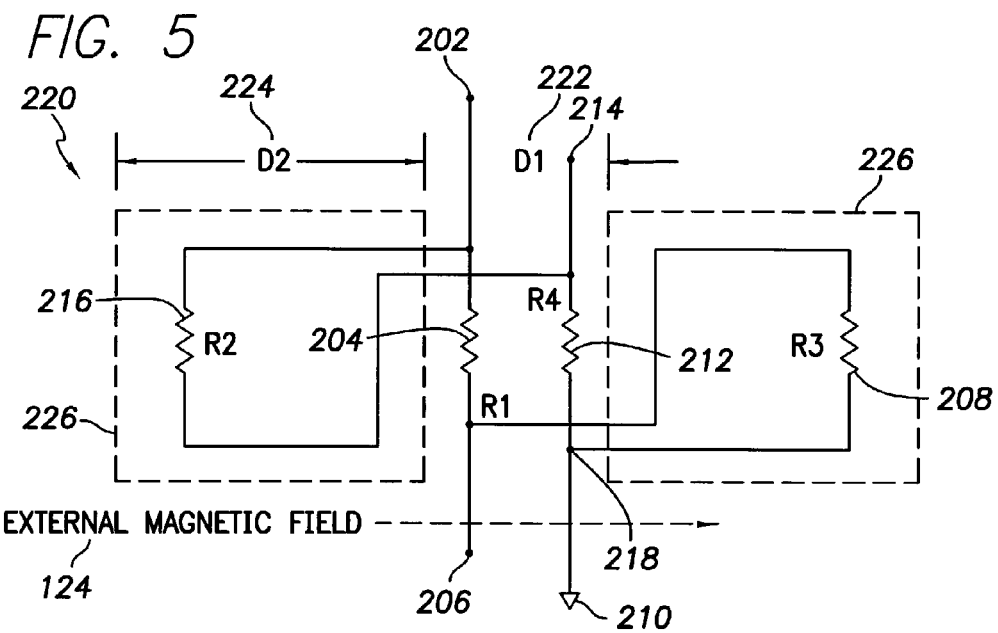
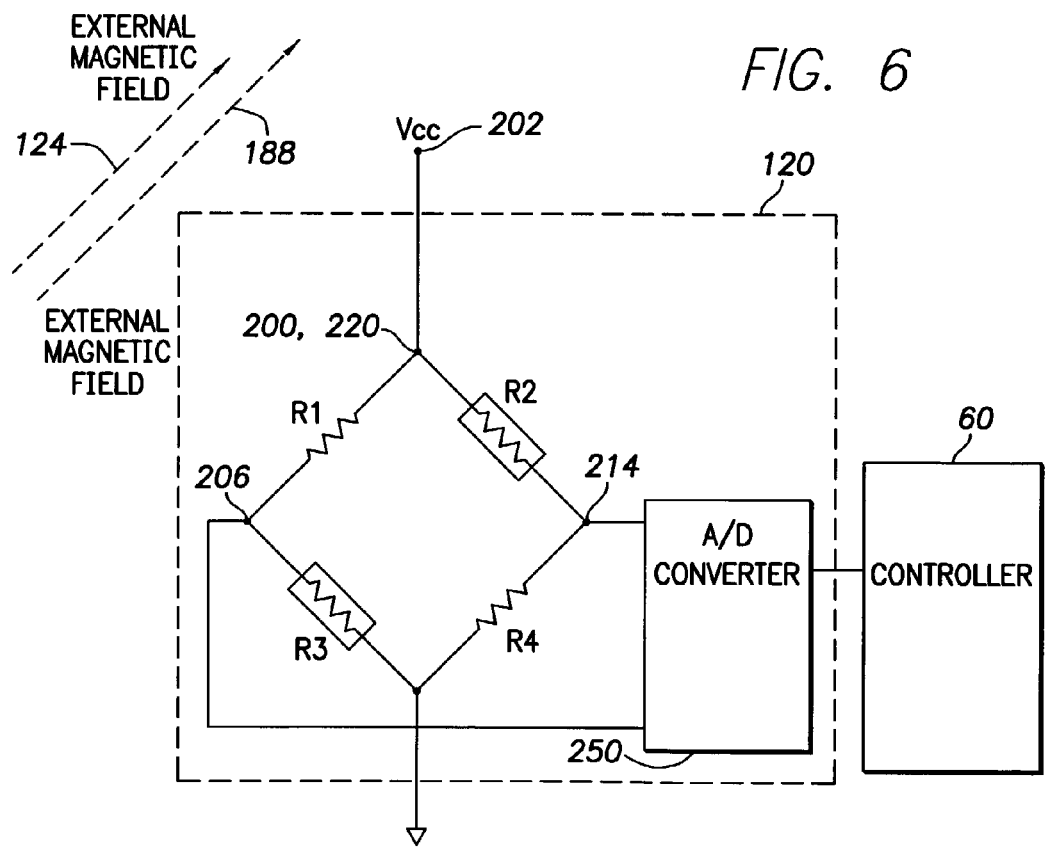

SYSTEM FOR THE SELECTIVE ACTIVATION OF FUNCTIONS IN AN IMPLANTABLE DEVICE BY A MAGNETIC FIELD

FIELD OF THE INVENTION

The present invention relates to implantable medical devices and, in particular, concerns an implantable cardiac stimulation device, whereby an induced external magnetic field can be used to activate selected functions of the implanted device.

BACKGROUND OF THE INVENTION

Implantable medical devices are being increasingly used to treat medical conditions. These types of devices include pacemakers, implantable cardioverter defibrillators, insulin pumps and the like. Being implanted, these devices are capable of providing therapy directly to the patient on a periodic or continuous basis. These devices are typically battery powered and are susceptible to battery failure over time. One class of commonly used implantable medical devices is implantable cardiac stimulation devices, such as pacemakers and implantable cardioverter defibrillators.

Implantable cardiac stimulation devices are typically implanted within the body cavity of a patient to monitor heart activity and provide therapeutic stimuli to treat a variety of medical conditions. Typically, cardiac stimulation devices monitor the beating of the heart and provide artificial stimulation to the heart to override brady/tachycardia and other arrhythmias as well as to interrupt fibrillation. These devices generally include circuitry for sensing heart function as well as circuitry and sensors that detect physiologic conditions of the patient. Conventionally, implantable cardiac stimulation devices comprise a variety of electronic components such as a limited power source, e.g. a battery, sensing circuits, stimulation circuits, a microcontroller, resistors, and capacitors, which are encapsulated within a small, biocompatible, hermetically sealed enclosure which protects the internal circuitry of the implantable cardiac stimulation device.

Once the implantable cardiac stimulation device has been assembled and is ready for patient implantation, the device is powered-up, and the individual circuit components of the device begin consuming battery power. This consumption of battery power often begins prior to actual implantation as the device is often enabled during final assembly. This power up of the device prior to implantation can significantly reduce the overall effective life of the device. Ultimately, the overall useful life of the cardiac stimulation device for the end user is minimized due to a reduced battery life and an inefficient technique of power consumption by the device. As a result, the implantable cardiac stimulation device has a limited shelf life prior to patient implantation.

Implantation of the cardiac stimulation device is an invasive procedure that often involves surgical entry into the body cavity of the patient. Such invasive surgical implantation procedures are physically demanding for the patient. Consequently, replacement of the implanted device due to impending battery failure results in the risk and discomfort to the patient. Therefore, extending the useful life of the implantable cardiac stimulation device would significantly reduce the amount of surgeries that a patient would undergo just to replace exhausted batteries.

Another aspect of implantable cardiac stimulation devices is that they may be designed and equipped with the ability to selectively activate a particular feature, function, or mode of operation with the use of a magnetic field sensor switch. Traditionally, these magnetic sensor devices employ a known reed switch that can be mechanically closed with the exposure of the reed switch to a magnetic field of a given threshold value. For example, one method of retrieving information recorded by the cardiac stimulation device is by a known wireless communication link, such as a telemetry circuit, from the implanted device to an external receiver, wherein an integrated telemetry circuit is utilized to transmit recorded monitoring data through body tissue to an external receiver via radio frequency transmission. Typically, the telemetry circuit is enabled through the use of a reed switch. This allows a medical professional to activate the downloading of the data stored in the device by positioning a magnet outside the patient's body proximate the implanted device. The reed switch is then triggered which results in a signal being sent to the implanted device enabling the telemetry circuitry.

Unfortunately, reed switches can be unreliable in operation. Typically, reed switches employ mechanical contacts, wherein mechanical failure is induced by a contact bounce, which may result in false contact readings. In addition, due to the function of the switch relying upon a mechanical occurrence, i.e., the mechanical movement of the reeds in response to the applied external magnetic field, variations in the material comprising the reeds may result in variations of performance of the reed switch. Hence, in some circumstances, the application of an external magnetic field may not result in the actuation of the reed switch in the desired fashion. Moreover, the repeated actuation of the reed switch may result in mechanical fatigue in at least one of the reeds to the point where the reed may become unreliable and inaccurate. Additionally, the reeds may occasionally remain stuck together after the application of the external magnetic field. In this circumstance, the reed switch may be continuously inducing the microcontroller to perform a specific function that is not needed thus inadvertently consuming power. This can also result in the reed switch no longer being capable of sensing future applications of the applied magnetic field. Furthermore, the mechanical movement required to provide a connection limits the overall switching effectiveness, response time, and reaction speed.

Moreover, reed switches are inherently designed to sense magnetic fields in any direction or magnitude thereof. Consequently, the reed switch may be accidentally triggered. This is the result of the inability of the reed switch to distinguish between magnetic fields of different magnitudes, when the magnitude is greater than an initial sensitivity threshold of the reed switch. Specifically, the patient may inadvertently be in a strong magnetic field, which could trigger the switch. For example, the strong magnetic field may be the result of the patient being around industrial equipment or undergoing a medical procedure such as magnetic resonance imaging (MRI). The inadvertent closing of the reed switch, in such a circumstance, may result in the implantable cardiac stimulation device switching to an undesired mode of operation or initiating an undesired function, which may also inadvertently consume power.

From the foregoing, there is a need for a device that permits activation of implantable medical devices, or activation of functions performed by implantable medical devices in a manner that is more reliable. To this end, there is a need for a device that allows for activation only when a specific magnetic field is detected and that is less likely to be inadvertently activated.

SUMMARY OF THE INVENTION

The aforementioned needs are satisfied by the implantable medical device of the present invention which, in one aspect, is comprised of a therapy delivery system that is adapted to deliver therapy to the patient when implanted in the patient. The device further includes a magnetic detector that detects the presence of an external magnetic field and produces a signal that has a magnitude that varies with the magnitude of the detected external magnetic field. The implantable medical device further includes a controller that receives a signal corresponding to the external magnetic field wherein the controller uses the signal to initiate a preselected function during operation of the implantable medical device when the magnitude of the detected external magnetic field corresponds to a preselected threshold.

In one specific implementation, the implantable medical device is comprised of an implantable cardiac stimulation device, such as a known pacemaker or implantable cardioverter defibrillator. The magnetic detector is comprised, in one implementation, of a Giant Magneto-Resistive (GMR)-based circuit that provides an analog voltage output that is indicative of magnitude of a sensed magnetic field. Since the controller is receiving a signal that is indicative of the magnitude of the sensed magnetic field, the controller can then discriminate between magnetic fields resulting from a selected magnet being positioned in proximity to the implantable medical device and spurious magnetic signals produced by other sources. Moreover, since the controller is receiving a signal that is indicative of the magnitude of the external magnetic field, the controller can be programmed to initiate a plurality of different functions in response to detecting a plurality of different magnetic fields. In this way, different functions, such as enablement of telemetry, enablement of recording of data, or other functions, can be initiated by positioning different magnets adjacent the implantable medical device.

In another aspect of the invention, the implantable medical device is configured to have a "quiescent" or "low power" state and a dynamic state. In the quiescent state, various amplifiers in the various sensors of the implantable medical device are not powered and the controller is operating in a rest condition where power consumption is reduced. In this particular configuration, the implantable medical device consumes less power than in an active or dynamic state wherein the implantable medical device is powered up for normal activity upon implantation. As a consequence, in the quiescent state, the implantable medical device is consuming less power from the battery, which thereby prolongs both the shelf life of the device and also the effective life of the device after implantation within the patient. In this particular aspect, the implantable medical device can be configured from the "quiescent" or "low power" state to the dynamic state by positioning a magnet, which has a particular selected magnetic field strength. The magnetic field detector provides a signal to the controller indicative of the existence of this magnet, causing the controller to power-up the device into the dynamic state.

From the foregoing, it will be appreciated that the use of a magnetic field detector that provides a signal that corresponds to the magnitude of detected external magnetic fields can be used to remotely initiate preselected functions within a hermetically sealed enclosure of an implantable or implanted medical device. These and other objects and advantages of the present invention will become more apparent from the following description taken in conjunction with the accompanying drawings.

BRIEF DESCRIPTION OF THE DRAWINGS

Further features and advantages of the present invention may be more readily understood by reference to the following description taken in conjunction with the accompanying drawings, in which:

FIG. 5 is a schematic illustration of an alternative embodiment of the Wheatstone Bridge GMR sensor, wherein supplemental metallic structures are utilized to improve the sensitivity of the magnetic field sensor;

FIG. 6 is a schematic illustration of a magnetic enablement circuit utilizing the magnetic field sensor of FIG. 4.

DETAILED DESCRIPTION OF THE PREFERRED EMBODIMENT

The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Figure 1:
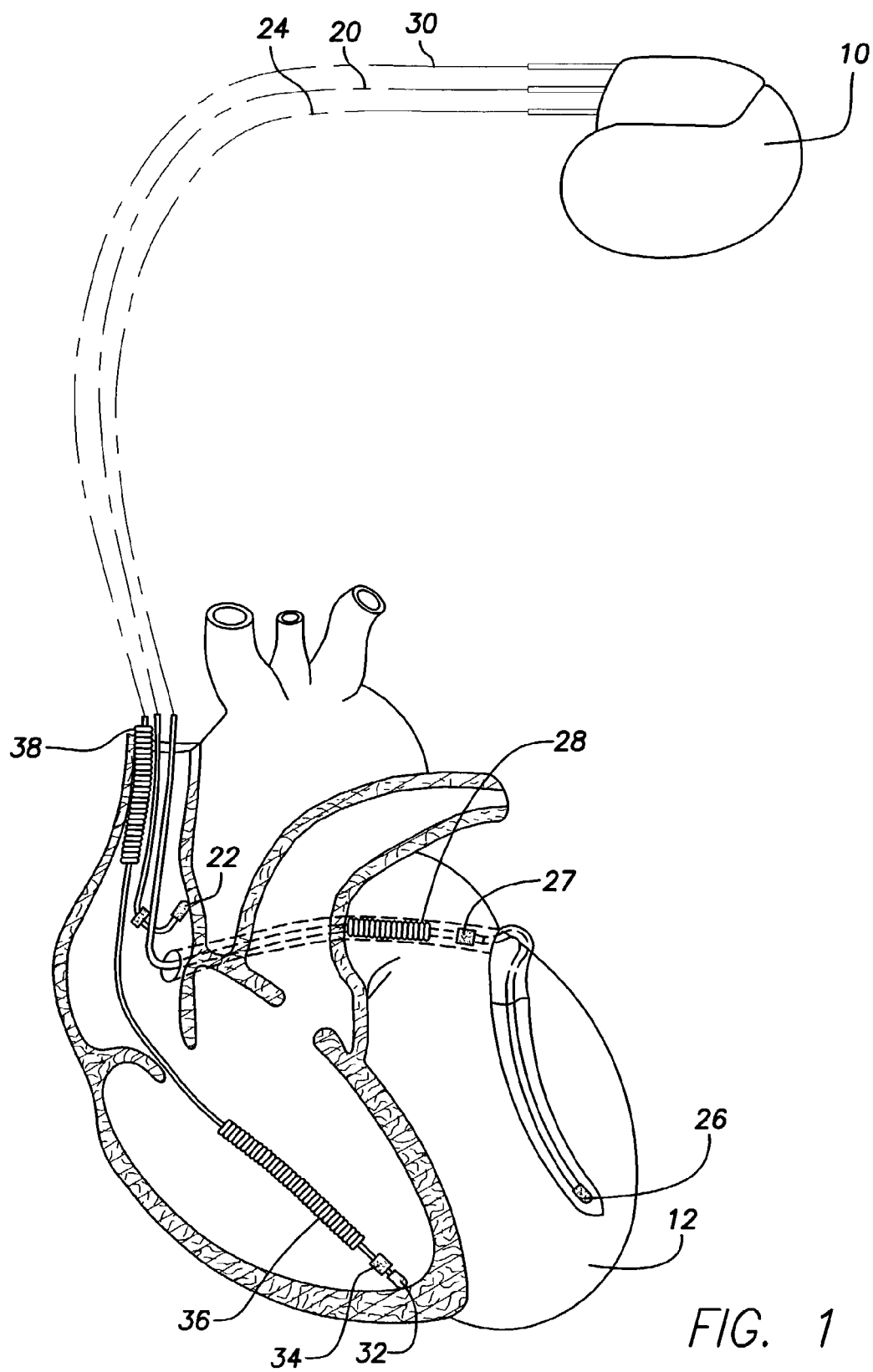
FIG. 1 is a simplified diagram illustrating an implantable stimulation device in electrical communication with at least three leads implanted into a patient's heart for delivering multi-chamber stimulation and shock therapy.

As shown in FIG. 1, there is a stimulation device 10 in electrical communication with a patient's heart 12 by way of three leads, 20, 24 and 30, suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage.

To sense left atrial and ventricular cardiac signals and to provide left chamber pacing therapy, the stimulation device 10 is coupled to a "coronary sinus" lead 24 designed for placement in the "coronary sinus region" via the coronary sinus os for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart 12 so as to place the right ventricular tip electrode 32 in the right ventricular apex so that the RV coil electrode will be positioned in the right ventricle and the SVC coil electrode 38 will be positioned in the superior vena cava. Accordingly, the right ventricular lead 30 is capable of receiving cardiac signals and delivering stimulation in the form of pacing and shock therapy to the right ventricle.

Figure 2:
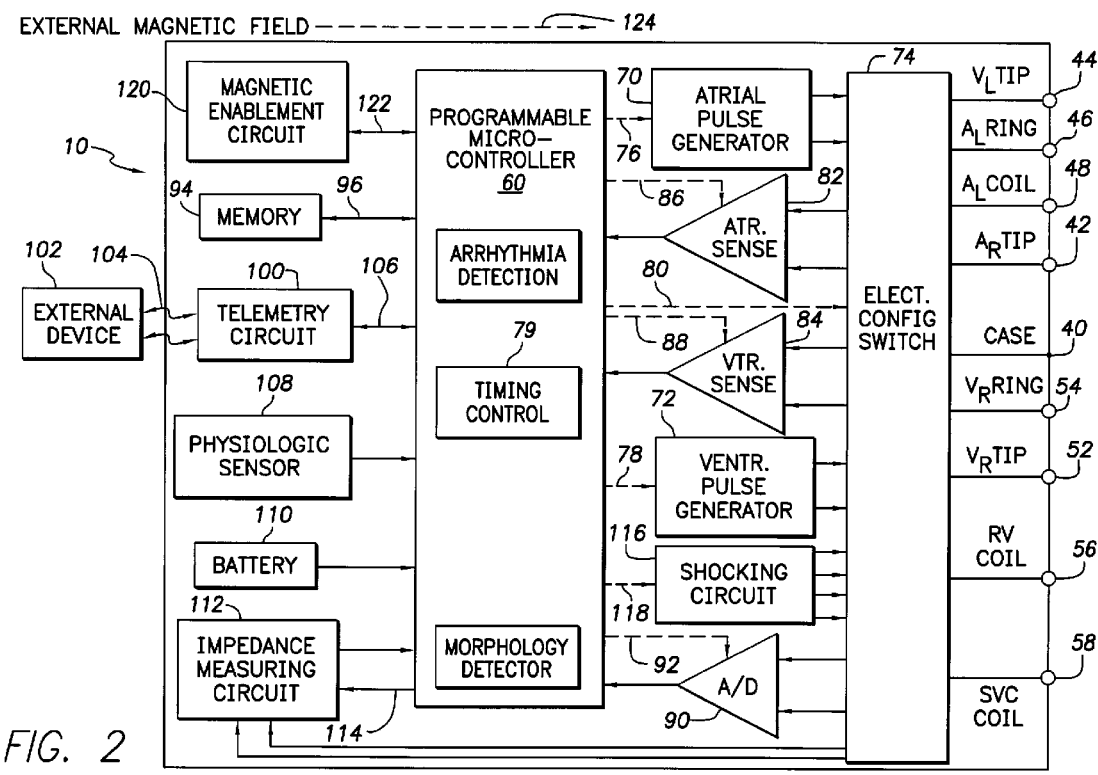
FIG. 2 is a functional block diagram of a multi-chamber implantable stimulation device illustrating the basic elements of a stimulation device which can provide cardioversion, defibrillation and pacing stimulation in four chambers of the heart.

In FIG. 2, a simplified block diagram is shown of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation, and pacing stimulation.

The housing 40 for the stimulation device 10, shown schematically in FIG. 2, is often referred to as the "can," "case," or "case electrode" and may be programmably selected to act as the return electrode for all "unipolar" modes. The housing 40 may further be used as a return electrode alone or in combination with one or more of the coil electrodes, 28, 36 and 38, for shocking purposes. The housing 40 further includes a connector (not shown) having a plurality of terminals, 42, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal ($A_R$ TIP) 42 adapted for connection to the atrial tip electrode 22.

To achieve left chamber sensing, pacing and shocking, the connector includes at least a left ventricular tip terminal ($V_L$ TIP) 44, a left atrial ring terminal ($A_L$ RING) 46, and a left atrial shocking terminal ($A_L$ COIL) 48, which are adapted for connection to the left ventricular ring electrode 26, the left atrial tip electrode 27, and the left atrial coil electrode 28, respectively. To support right chamber sensing, pacing and shocking, the connector further includes a right ventricular tip terminal ($V_R$ TIP) 52, a right ventricular ring terminal ($V_R$ RING) 54, a right ventricular shocking terminal ($R_V$ COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60, which controls the various modes of stimulation therapy. As is well known in the art, the microcontroller 60 typically includes a microprocessor, controller, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the present invention. Rather, any suitable microcontroller 60 may be used that carries out the functions described herein. The use of microprocessor-based control circuits for performing timing and data analysis functions are well known in the art.

Advantageously, the operating parameters of the implantable device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by a control signal 106 from the microcontroller 60, wherein the telemetry circuit 100 allows intracardiac electrograms and status information relating to the operation of the device 10, as contained in the microcontroller 60 or memory 94, to be sent to the external device 102 through an established communication link 104.

The stimulation device 10 further comprises a magnetic enablement circuit 120 coupled to the microcontroller 60, wherein the purpose of the magnetic enablement circuit 120 is to detect when a magnetic field 124 is in near proximity to the stimulation device 10. Application of a magnetic field 124, in one embodiment, may be used by a clinician to activate various test functions of the stimulation device 10 and/or to signal the microcontroller 60 that the external programmer 102 is in place to receive or transmit data to the microcontroller 60 through the telemetry circuit 100. Alternatively, the magnetic enablement circuit 120 may also be used to place the device into an active mode from a storage mode as will also be described in greater detail hereinbelow.

The magnetic enablement circuit 120 comprises activation control circuitry, wherein, in one embodiment, an externally applied magnetic field induces the activation of a plurality of control signals 122 to the microcontroller 60. As is also known in the art, magnetic field strength is a product of inherent characteristics of the magnetic device that produces the magnetic field. Therefore, depending on the magnetic device used and the composition thereof to produce the magnetic field, the strength of the magnetic field 124 will vary between different magnetic field generating devices.

As will be discussed below, it is possible to apply a plurality of different magnetic field strength magnitudes 124 to the magnetic field sensor of the magnetic enablement circuit 120, wherein the magnetic field strength magnitudes may be measured by a resistance differential between magneto-resistive elements of the sensor and compared, using a comparator, to a set of predetermined threshold values. These comparisons may be employed to generate a plurality of control signals 122 to the microcontroller 60. The microcontroller 60 can thereby receive and interpret the plurality of control signals 122 to activate features, functions, or modes of operation of the stimulation device 10. The magnetic field sensors comprised by the magnetic enablement circuit 120 will be further discussed herein below.

The stimulation device 10 additionally comprises a power source 110, such as a battery, which provides, in one embodiment, operating power to most of the circuit elements illustrated in FIG. 2. For the stimulation device 10, which may employ shocking therapy, the power source 110 must be capable of operating at low current drains for long periods of time, significantly less than 10 $\mu$A, and then be capable of providing high-current pulses, for capacitor charging, when the patient requires a shock pulse in excess of 2 A and at voltages above 2 V, for periods of 10 seconds or more. The power source 110 must also have a predictable discharge characteristic so that elective replacement time can be detected. Accordingly, the stimulation device 10, in one embodiment, employs lithium-silver-vanadium oxide batteries, as is true for most conventional implantable electronic stimulation devices.

In the case where power conservation is a factor for an increased operational longevity of the stimulation device 10, a power source 110 would benefit from an extended life by consuming power at two different rates: a normal operating rate and a rest rate. Under normal operating conditions, the stimulation device 10 operates at a normal operating rate upon activation. Prior to activation by a control signal 122 from the magnetic enablement circuit 120, the stimulation device 10 and the microcontroller 60 consume power at a rest rate, which is less than the normal operating rate. In addition, during the rest rate power consumption mode of operation, other stimulation device 10 elements consume significantly less power. Thus, a rest rate mode of operation extends the power source 110 life of use, which, in turn, extends the useful life of the stimulation device 10.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control circuitry 79 which is used to control the timing of such stimulation pulses (e.g., pacing rate, atrio-ventricular (AV) delay, atrial interconduction (A—A) delay, or ventricular interconduction (V—V) delay, etc.) as well as to keep track of the timing of refractory periods, blanking intervals, noise detection windows, evoked response windows, alert intervals, marker channel timing, etc., which is well known in the art.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers, or shared amplifiers. The switch 74 determines the "sensing polarity" of the cardiac signal by selectively closing the appropriate switches, as is also known in the art. In this way, the clinician may program the sensing polarity independent of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart. The sensing circuits, 82 and 84, in turn, receive control signals over signal lines, 86 and 88, from the microcontroller 60 for purposes of controlling the gain, threshold, polarization charge removal circuitry (not shown), and the timing of any blocking circuitry (not shown) coupled to the inputs of the sensing circuits, 82 and 84, as is known in the art.

For arrhythmia detection, the device 10 utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") (the preference here is to use "atrial Fib-waves" and "ventricular Fib-waves" to make the specifications more readable, instead of just "F-waves" or even "$F_A$-waves") (at least until such time that it becomes a generally used term) are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (A/D) data acquisition system 90. The data acquisition system 90 is configured to acquire intracardiac electrogram signals, convert the raw analog data into digital signals, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy.

In one embodiment, the stimulation device 10 further includes a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states).

Accordingly, the microcontroller 60 responds by adjusting the various pacing parameters (such as rate, AV Delay, V—V Delay, etc.) at which the atrial and ventricular pulse generators, 70 and 72, generate stimulation pulses.

As further shown in FIG. 2, the device 10 is shown as having an impedance measuring circuit 112 which is enabled by the microcontroller 60 via a control signal 114. The known uses for an impedance measuring circuit 112 include, but are not limited to, lead impedance surveillance during the acute and chronic phases for proper lead positioning or dislodgment; detecting operable electrodes and automatically switching to an operable pair if dislodgment occurs; measuring respiration or minute ventilation; measuring thoracic impedance for determining shock thresholds; detecting when the device has been implanted; measuring stroke volume; and detecting the opening of heart valves, etc. The impedance measuring circuit 112 is advantageously coupled to the switch 74 so that any desired electrode may be used. The impedance measuring circuit 112 is not critical to the present invention and is shown only for completeness.

In the case where the stimulation device 10 is intended to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 Joules), moderate (0.5–10 Joules), or high energy (11 to 40 Joules), as controlled by the microcontroller 60. Such shocking pulses are applied to the patient's heart 12 through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5–40 Joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

As discussed above, the implantable cardiac device includes a magnetic enablement circuit 120 that can be used to either selectively enable functions of the circuitry of the implanted device 10 by placing a magnet having a preselected magnitude in proximity to the device 10. As such, the functionality of an implanted device can be altered in a simple and non-invasive manner. Moreover, the circuitry inside the hermetically sealed enclosure can also be enabled or otherwise programmed from outside the sealed enclosure. As will be described in greater detail below, the magnetic enablement circuit 120 includes a sensor that provides a variable output that varies depending upon the detected intensity of the magnetic field. This allows for easier filtering of spurious magnetic fields and it also allows for the enablement circuit 120 to provide signals that can enable multiple different functions. These features will be described in greater detail below.

Figure 3:
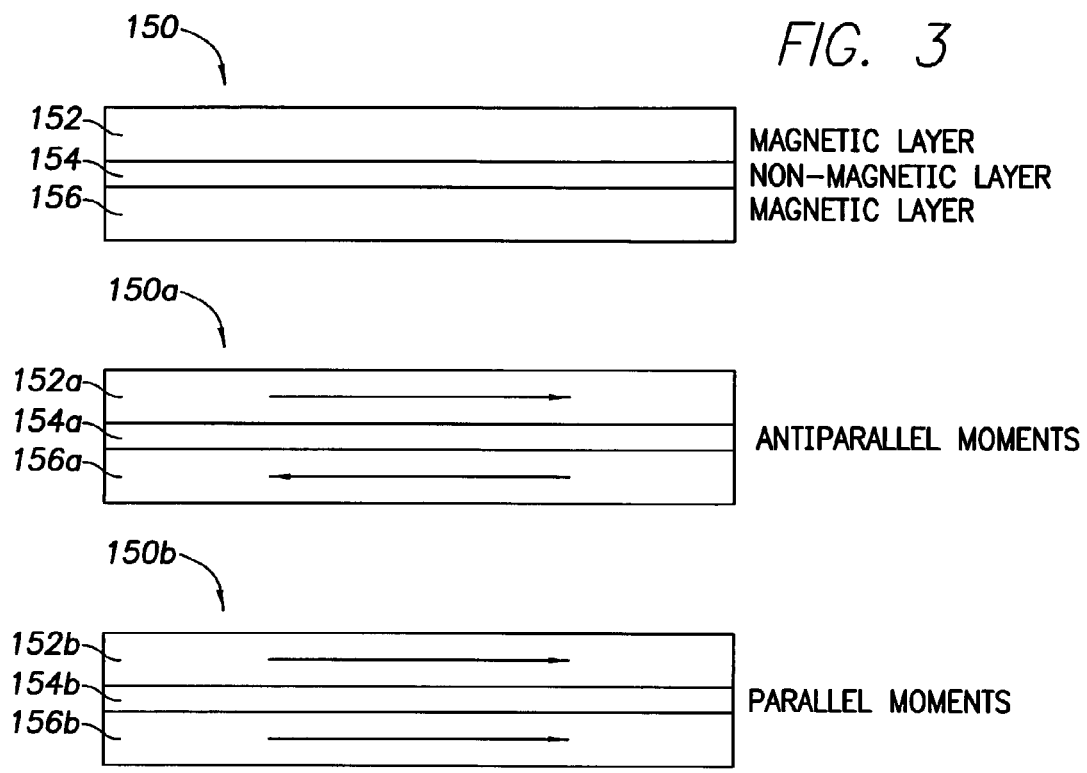
FIG. 3 is a diagram that illustrates the individual stacked layers of a GMR device.

In the preferred embodiment, the magnetic enablement circuit 120 includes Giant Magnetoresistive (GMR) resistors. FIG. 3 is a schematic illustration illustrating the typical operation of these types of devices. As illustrated, a typical GMR resistor 150 comprises a non-magnetic "tunnel" layer 154 interposed between two magnetic layers 152 and 156. With the application of a magnetic field, the resistance differential across the GMR resistor 150 may be altered by realigning the moments of the magnetic layers 152*a* and 156*a* into a parallel or antiparallel state. A GMR resistor 150*a* with magnetic layers 152*a* and 156*a* of parallel magnetic moments provides less scattering of electrons traversing the GMR resistor 150*a*, which results in a lower resistance differential across the GMR resistor 150*a*. Conversely, a GMR resistor 150*b* with magnetic layers 152*b* and 156*b* of antiparallel magnetic moments provides a significant increase in the scattering of electrons traversing the GMR resistor 150*b*, which results in a high differential resistance across the GMR resistor 150*b*. The degree of scattering is dependent on the intensity and direction of the magnetic field. Hence, the resistance of the material is variable over a range of values, which can result in a control signal that also has a predictable range.

Figure 4:
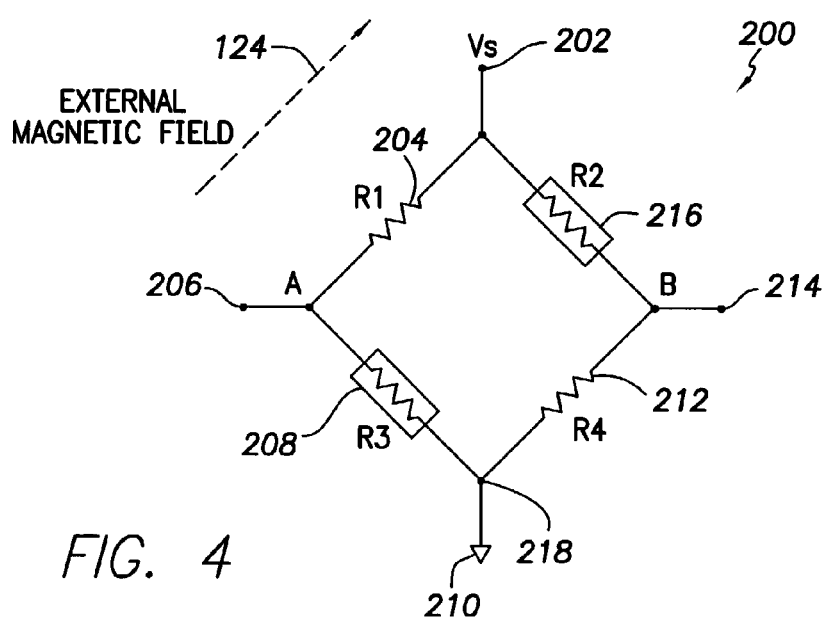
FIG. 4 is a schematic illustration of a GMR magnetic field sensor, wherein a plurality of GMR devices, configured into a Wheatstone Bridge, are utilized in the sensor device.
Figure 7:
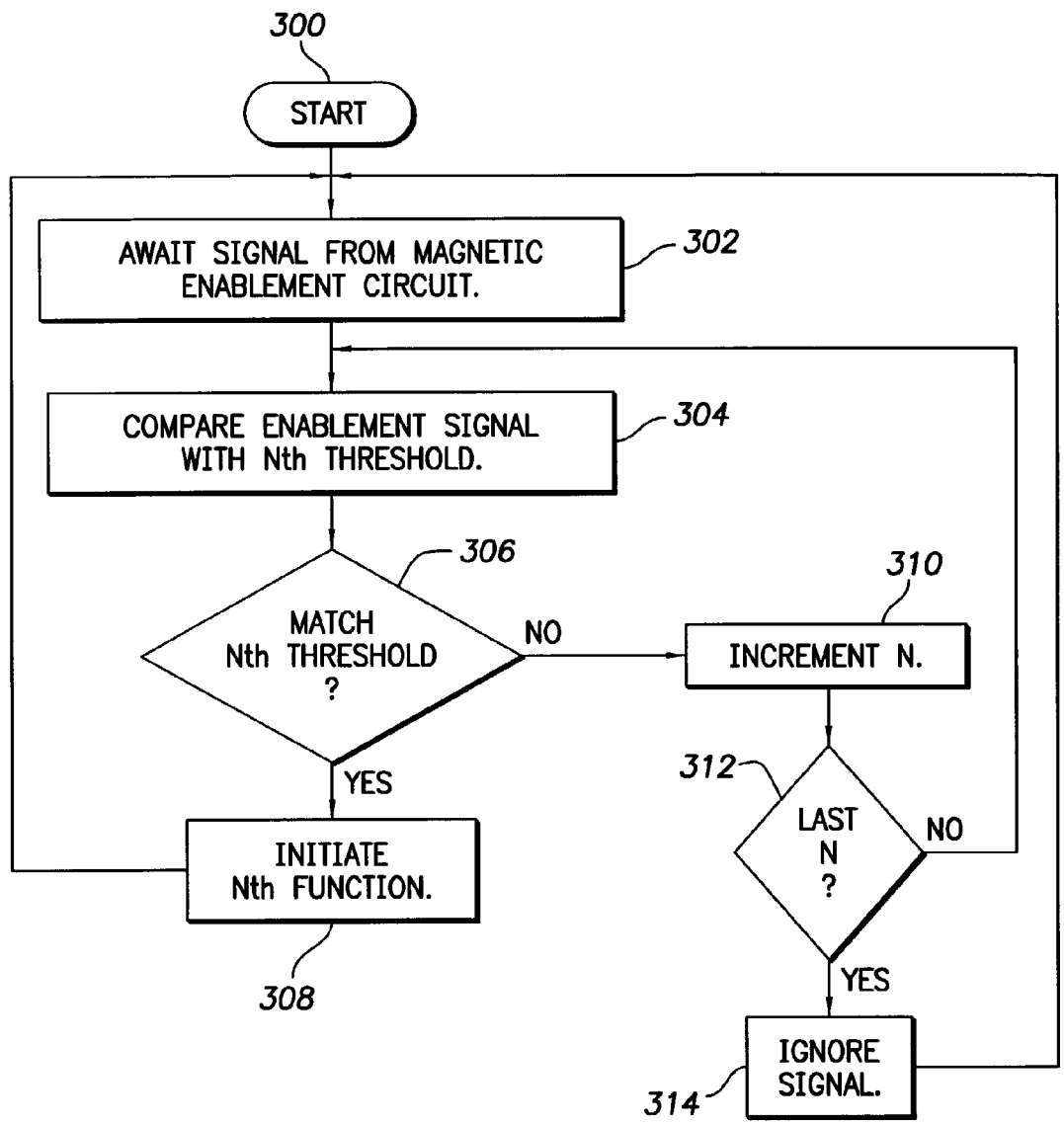
FIG. 7 is a flow chart illustrating the operation of the magnetic enablement circuit and controller of FIG. 2.

As shown in FIG. 4, a magnetic field sensor 200 utilizing GMR resistors is preferably arranged into a Wheatstone Bridge configuration for improved sensitivity. A highly sensitive Wheatstone Bridge sensor may be fabricated from four photolithographically formed GMR resistors, 204, 208, 212, and 216, (such as those illustrated in FIG. 3) wherein GMR resistors 204 and 212 are magnetically active elements, and GMR resistors 208 and 216 are shielded from magnetic field interference.

In one possible implementation, the GMR resistors 204, 208, 212, and 216 are approximately 2 microns in width and 100 microns in length, and they are deposited and patterned in a manner known in the art. The narrow width of the active GMR resistors 204 and 212 confines the magnetic field sensitivity to the component of the magnetic field along their long dimension, and the narrow width provides a significant immunity to traversing magnetic fields. The magnetically shielded GMR resistors 208 and 216 act as reference resistors when calculating resistance differentials between resistors at nodes 206 and 214. The four GMR resistors 204, 208, 212, and 216 are fabricated from the same material, which preserves significantly similar performance characteristics, such as temperature coefficients, of the GMR resistors, 204, 208, 212, and 216.

The sensing of a resistance differential, in one embodiment, is as follows from the Wheatstone Bridge device 200 of FIG. 4. A voltage source ($V_S$) is applied at a node 202, and a common ground link 210 is attached to a node 218. When a magnetic field is applied along the long dimension of the active resistors, 204 (R1) and 212 (R4), the resistance changes, but the shielded resistors, 208 (R3) and 216 (R2), remain unaffected by the applied magnetic field 124. In this case, the voltage potential ($V_A$) at a node (A) 206 is substantially different than the voltage potential ($V_B$) at node (B) 214, which results in the sensing of a voltage differential induced by a magnetic field. The voltage differential is sensed by a comparator (not shown), which is further described herein below, and calculated by the employment of a known voltage divider circuit:

$$V_A = V_S\left(\frac{R_3}{R_1 + R_3}\right) \quad V_B = V_S\left(\frac{R_4}{R_2 + R_4}\right)$$

FIG. 5 schematically illustrates an alternative embodiment of the Wheatstone Bridge magnetic field sensor device 220, wherein flux concentrators 226 are plated, by a deposition technique known in the art, significantly adjacent to the shielded resistors, 208 and 216. The active resistors, 204 and 212, are formed in the gap between the flux concentrators 226, wherein the sensed magnetic field 124 is experienced with an increased magnitude by which the factor is approximately the ratio of the gap length (D1) 222 and the flux concentrator length (D2) 224. An advantage to utilizing this embodiment is that the sensitivity threshold of a magnetic field sensor 220 may be adjusted to desired parameters by varying the gap length 222 and the flux concentrator length 224. The resistance differential for the magnetic field sensor 220 is magnetically sensed in the same manner as previously described for the magnetic field sensor 200.

Applications involving the magnetic field sensors, 200 and 220, include voltage and current regulation and magnetic field strength sensing through threshold detection to provide a switched output when a predetermined threshold value is reached. The magnetic field sensor 220 configuration is a desired embodiment in that it may be calibrated to sense specifically desired threshold parameters when parallel to specific magnetic moments. As a result, the GMR resistors, 204 and 212, significantly respond to the moment of the magnetic field along their longest physical dimension. Furthermore, the narrow width of the GMR resistors, 204 and 212, provide a significant immunity to traversing magnetic fields, which increases reliability and accuracy.

The magnetic field sensors 200, 220 therefore provide an output signal that is proportionate to the magnitude and direction of the sensed magnetic field. Hence, by positioning magnets having a known magnitude and direction in proximity to the cardiac stimulation device, a known voltage signal can be produced by the magnetic field sensor 200, 220.

FIG. 6 illustrates an example of the magnetic enablement circuit 120 that can be used to provide a plurality of control signals to the microprocessor or microcontroller 60 of the implantable cardiac device. As is illustrated in FIG. 6, the magnetic field sensor 200, 220 produces a differential voltage output signal from the nodes 206, 214 which is then provided to an Analog to Digital (A/D) converter 250. The A/D converter 250 then provides a digital signal 251 to the microcontroller 60. The digital signal is representative of the magnitude of the differential output voltage that is being provided by the magnetic field sensor 200, 220.

The microcontroller 60 can then incorporate a software routine that compares the digital signal from the A/D converter 250 to predetermined threshold values or ranges to determine if a sensed magnetic field corresponds to the magnetic fields 124, 188 that are created by a particular selected magnet. In this way, the microcontroller 60 can determine if a sensed magnetic field is a preselected magnetic field that is being directed towards the device 10 in order to induce the device 10 to initiate some preselected function. While FIG. 6 discloses the use of an A/D converter for providing a digital signal to the microcontroller 60, it will be appreciated that any of a number of different implementations can be used to provide signals to the microcontroller 60 representative of the magnitude of the sensed magnetic field. For example, comparators and other similar hardware can also be used to determine whether the sensed magnetic field is within the appropriate threshold range without departing from the spirit of the present invention.

Since the magnetic field sensors 200, 220 are providing a voltage value that is then compared to a preselected threshold value or range, the ability of the microcontroller 60 to discriminate between spurious magnetic signals and signals emanating from the first or second magnet is enhanced. In one implementation, a range of values can be set for a particular function. If a weaker or stronger magnetic field is present, the magnetic field sensors 200, 220 will not provide a signal within a preselected range and those magnetic fields will not induce the microcontroller 60 to initiate any additional functions.

In one embodiment, a first function comprises a power-up activation sequence. A power supply that provides power to the implantable cardiac stimulation device may initially operate and consume power at a "low power" or "quiescent" rate. Upon a power-up activation signal provided by the magnetic enablement circuit 120 to the microcontroller 60 as a result of positioning a magnet having a preselected magnetic field strength in proximity to the hermetically sealed enclosure, the device may operate and consume power at a normal operating rate, which is significantly more than the power consumption rate of the "low power" or "quiescent" rate. The advantage to utilizing two different operating rates is that power may be initially conserved prior to the power-up activation sequence, which extends the useful life of the power source concurrently with extending the useful life of the device itself. Typically, when implantable medical devices, such as implantable cardiac stimulation devices, are manufactured, they are enabled which results in consumption of limited battery power prior to implantation. Having a function that allows remote activation of the device from a "low power" or "quiescent" rate to a normal operating rate at implantation, results in power being conserved prior to implantation thereby providing more available power after implantation which prolongs the effective life of the implanted device.

In another embodiment, the second function may comprise an activation sequence of the telemetry circuit 100. A particular magnet may be employed by the treating medical professional to produce a magnetic field that results in a signal being provided to the microcontroller 60 that induces activation of the telemetry signal for subsequent downloading of information to an external programmer. Upon a telemetry activation signal being provided by the magnetic enablement circuit to the microcontroller 60, the telemetry circuit 100 is then, in turn, activated by the microcontroller 60 by a control signal. The telemetry circuit 100 permits intracardiac electrograms and status information relating to the operation of the stimulation device 10 to be transmitted to the external device 102 through an established communication link 104. Also, the operating parameters of the implantable device 10 may be non-invasively programmed into the memory 94 through a telemetry circuit 100 in telemetric communication with the external device 102, such as a programmer or a diagnostic system analyzer. The advantage gained is that the telemetric switching reliability and accuracy is increased due to the significantly improved magnetic field sensor 200, 220.

In yet another embodiment, the second function may comprise a recording function. In some circumstances, it may be desirable for the implantable cardiac stimulation device 10 to record heart activity in the memory 94 for further downloading to an external programmer for subsequent review and analysis. Typically, the memory capacity of the implanted device is often limited so it is not generally possible to record signals of all heart activity during the period between following visits. In this implementation, when the patient feels an abnormal heart activity, they can use a magnet having a preselected strength to induce the microcontroller 60 to record the heart signal in the memory 94. Again, the use of the GMR circuit reduces the likelihood that spurious magnetic signals will result in the microcontroller 60 recording heart signals unnecessarily.

FIG. 6 is a flow chart that illustrates the operation of the microcontroller 60 as it receives signals from the magnetic enablement circuit 120. From a start state 300, the microcontroller 60 then awaits a signal from the magnetic enablement circuit 120 in state 302. As discussed above, the magnetic field sensor 200, 220 provides an analog signal to the A/D converter 250 which then provides the controller a signal that corresponds to the analog voltage differential signal detected by magnetic field sensor 200, 220. Hence, the microcontroller 60 receives a signal indicative of the magnitude of each of the sensed magnetic fields.

Once a magnetic field is detected, the microcontroller 60 then compares, in state 304, the magnitude of the signal to an Nth preselected threshold range. The microcontroller 60 then determines, in decision state 306, whether the detected magnetic field is within the Nth preselected threshold range. As discussed above, the A/D converter is providing a specific signal indicative of the magnitude of the sensed magnetic field. The microcontroller 60 compares this specific signal to signals stored in the memory to determine whether a preselected magnet has been positioned in proximity to the device 10.

If the microcontroller 60 determines that the signal received from the magnetic enablement circuit 120 corresponds to the Nth stored value, then the microcontroller 60 initiates the corresponding Nth function in state 312. As discussed above, the Nth function can be comprised of any of a number of functions including a power up function, a recording function or a telemetry function.

If the microcontroller 60 determines that the signal received from the magnetic enablement circuit 120 does not correspond to the Nth stored value the microcontroller 60 then it increments N, in state 310, and then compares the magnetic enablement signal to the next stored threshold value. The process comprising the steps 304, 306 and 310 is repeated for each possible stored function value until the microcontroller 60 determines, in decision state 312, that the signal received from the magnetic enablement circuit 120 does not correspond to any of the signals for functions stored in the memory, in which case, the microcontroller 60 ignores the signal in state 314 and returns to state 302 to await the next signal.

Hence, the implantable medical device 10 incorporating the GMR based magnetic field sensor is capable of distinguishing between a plurality of different magnetic fields and determining whether any of the magnetic fields correspond to a particular magnetic field to initiate a particular function. Thus, the magnetic enablement circuit 120 can filter out spurious signals better and can also allow for multiple functions to be enabled by multiple different magnets. It will be appreciated that the microcontroller 60 can also be programmed to only initiate particular functions when a preselected pattern of magnetic fields is sensed without departing from the spirit of the present invention.

GMR configured magnetic field sensors used for switching offer significant advantages for the activation of selectable features, functions, and modes of operation. GMR magnetic field sensor applications to implantable stimulation devices, where sensitivity, reliability, accuracy, and small size are important characteristics to the devices, exhibit improved digital switching with firmly controlled magnetic operation and release points. Further advantages include reduced power consumption by the device, faster response rates, solid state reliability, and reverse power source protection. Another benefit to utilizing GMR configured magnetic field sensing switches is that magnetic fields of reasonable strength have no known injurious effects on the human body or tissue thereof. In addition, magnetic fields are significantly non-invasive and readily traverse the body cavity to the implanted electronic device without patient discomfort. Therefore, the sensing of magnetic field magnitudes and strengths present an efficient method for feature, function, and mode of operation activation.

Although the above described embodiments of the present invention have described, illustrated, and characterized the fundamental novel features of the invention as applied to those embodiments, it will be understood that various omissions, substitutions, and changes in the form of the detail of the device represented may be made by those skilled in the art without departing from the spirit of the present invention. Consequently, the scope of the invention should not be limited to the foregoing description but is to be defined by the appended claims.

What is claimed is:

1. An implantable cardiac stimulation device that provides electrical stimulation to a patient's heart, the device comprising:
   a power supply;
   a pulse generating circuit that produces the electrical stimulation;
   a magnetic enablement circuit that provides a signal when detecting an external magnetic field, wherein at least one parameter of the signal varies with a magnitude of the detected external magnetic field;
   a sensor device that senses heart function and provides a heart signal indicative thereof;
   a controller that receives the heart signal from the sensor device and induces the pulse generating circuit to provide the electrical stimulation when the controller determines that the heart is in need of the electrical stimulation, and wherein the controller receives the signal from the magnetic enablement circuit and, if the at least one parameter of the signal corresponds to a first value, the controller initiates a first preselected function, and if the at least one parameter of the signal corresponds to a second value, the controller initiates a second preselected function.

2. The device of claim 1, wherein the first preselected function is a power-up activation sequence.

3. The device of claim 1, wherein the second preselected function is a telemetry activation sequence.

4. The device of claim 1, wherein the second preselected function is a recording activation sequence.

5. The device of claim 1, wherein the magnetic enablement circuit comprises a GMR based magnetic field sensor that provides an output signal indicative of the magnitude of the sensed magnetic field.

6. The device of claim 5, wherein the magnetic field sensor includes a plurality of GMR resistors wherein at least one of the GMR resistors are shielded and wherein the plurality of GMR resistors are connected together so as to produce a signal that is proportionate to the magnitude and direction of the magnetic field.

7. The device of claim 6, wherein the magnetic enablement circuit further includes an analog to digital converter that receives the output signal from the magnetic field sensor and provides a digital signal to the controller for the controller to determine whether the signal corresponds to the first or the second threshold.

8. An implantable medical device that provides stimulation therapy to a patient, the device comprising:
- a therapy delivery system;
- a magnetic enablement circuit that includes a magnetic field sensor that provides an activation signal when exposed to a magnetic field of a selected threshold;
- a controller that receives signals from the magnetic enablement circuit and provides signals to the therapy delivery system so as to induce the therapy delivery system to provide stimulation therapy to the patient and wherein the controller activates the implantable medical device upon receipt of the activation signal from the magnetic enablement circuit;
- a power supply that provides power to the therapy delivery system and the controller, wherein the controller and the therapy delivery system consume power at a normal operating rate upon activation and wherein the controller and the therapy delivery system consume power at a reduced rate, which is less than the normal operating rate prior to activation of the device to thereby conserve power prior to activation of the implantable medical device.

9. The device of claim 8, wherein the activation signal provided by the magnetic enablement circuit has a magnitude that corresponds to the magnitude of the magnetic field sensed by the magnetic field sensor.

10. The device of claim 9, wherein the magnetic field sensor comprises a GMR sensor.

11. The device of claim 10, wherein the controller activates the implantable medical device upon receiving an activation signal indicating that the enablement magnetic circuit had detected a magnetic field having a preselected magnitude.

12. The device of claim 8, wherein the controller has a normal operating mode and a reduced operating mode and wherein the controller enters the normal operating mode from the reduced operating mode upon receipt of the activation signal from the magnetic enablement circuit.

13. The device of claim 8, further comprising a physiologic sensor that senses a physiologic condition of the patient, wherein the physiologic sensor in the reduced operating mode does not receive power from the power supply and wherein the physiologic sensor in the normal operation mode receives power from the power supply.

14. An implantable medical device that provides stimulation therapy to a patient, the device comprising:
- a therapy delivery system that is adapted to deliver therapy to the patient when implanted in the patient;
- a magnetic field sensor that detects the presence of an external magnetic field and produces a magnetic signal that has a magnitude that varies with the magnitude of the detected external magnetic field;
- a controller that receives a signal corresponding to the magnetic signal wherein the controller uses the signal to initiate a first preselected function in response to detection of a first magnetic field having a first magnitude and a second preselected in response to detection of a second magnetic field having a second magnitude during operation of the implantable medical device.

15. The device of claim 14, wherein the therapy delivery system comprises a lead that is adapted to be positioned adjacent the wall of the patient's heart and a electrical generating circuit that produces electrical stimulation configured to stimulate the heart of the patient when delivered through the lead.

16. The device of claim 15, further comprising at least one sensor device that senses heart function and provides a heart signal indicative thereof to the controller.

17. The device of claim 14, wherein the magnetic field sensor provides a first magnetic signal when sensing the presence of a first magnetic field occurring as a result of a first magnet being positioned adjacent the implanted medical device.

18. The device of claim 16, wherein the magnetic field sensor comprises a GMR circuit and an A/D converter that provides a digital signal indicative of the magnitude of the detected magnetic field to the controller and wherein the controller determines whether the detected magnetic field corresponds to a predetermined magnetic field to thereby initiate a preselected function.

19. The device of claim 18, wherein one of the preselected functions comprises initiating a normal operation state of the implantable medical device from a rest state.

20. The device of claim 18, wherein one of the preselected functions comprises initiating a recording function whereby heart signals from the at least one sensor are recorded by the controller.

21. An implantable medical device that provides stimulation therapy to a patient, the device comprising:
- means for delivering therapy to the patient when implanted in the patient;
- means for detecting the presence of an external magnetic field;
- means for producing a magnetic field signal that has at least one parameter that varies with the magnitude of the detected external magnetic field;
- means for initiating a first preselected function in response to a first magnetic field signal having a first parameter value and a second preselected function in response to a second magnetic field signal having a second parameter value.

22. The device of claim 21, wherein the means for delivering therapy to the patient comprises a lead that is adapted to be positioned adjacent the wall of the patient's heart and an electrical generating circuit that produces electrical stimulation configured to stimulate the heart of the patient when delivered through the lead.

23. The device of claim 22, further comprising means for sensing heart function and providing a heart signal indicative thereof to the controller.

24. The device of claim 23, wherein the means for detecting the external magnetic field provides a first magnetic signal when sensing the presence of a first magnetic field occurring as a result of a first magnet being positioned adjacent the implanted medical device.

25. The device of claim 24, wherein the means for detecting the external magnetic field comprises a GMR circuit and an A/D converter that provides a digital signal indicative of the magnitude of the detected magnetic field to the controller and wherein the controller determines whether the detected magnetic field corresponds to a predetermined magnetic field to thereby initiate a preselected function.

26. The device of claim 25, wherein one of the preselected functions comprises initiating a normal operation state of the implantable medical device from a rest state.

27. The device of claim 25, wherein one of the preselected functions comprises initiating a recording function whereby detected patient parameters are recorded by the controller.

28. In an implantable cardiac stimulation device, a method comprising:
 detecting an external magnetic field;
 determining a magnitude of the external magnetic field; and
 initiating a first preselected function in response to detection of an external magnetic field having a first magnitude and a second preselected function in response to detection of an external magnetic field having a second magnitude.

29. The device of claim 1, wherein the parameter of the signal comprises one of a magnitude, a pulse width, a phase and a frequency of the signal.

* * * * *